US009274053B2

(12) United States Patent
Escobedo et al.

(10) Patent No.: US 9,274,053 B2
(45) Date of Patent: Mar. 1, 2016

(54) FLOW THROUGH METALLIC NANOHOLE ARRAYS

(75) Inventors: Carlos Escobedo, Victoria (CA); David A. Sinton, Victoria (CA); Reuven Gordon, Victoria (CA); Alexandre Brolo, Close (CA)

(73) Assignee: UVic Industry Partnerships Inc., Victoria (CA)

( * ) Notice: Subject to any disclaimer, the term of this patent is extended or adjusted under 35 U.S.C. 154(b) by 0 days.

(21) Appl. No.: 13/110,598

(22) Filed: May 18, 2011

(65) Prior Publication Data

US 2012/0292496 A1    Nov. 22, 2012

(51) Int. Cl.
*H01J 49/00*    (2006.01)
*G01N 21/552*    (2014.01)
(Continued)

(52) U.S. Cl.
CPC ........ *G01N 21/554* (2013.01); *G01N 33/54373* (2013.01); *B01L 3/502761* (2013.01)

(58) Field of Classification Search
CPC .................. C12Q 2565/628; C12Q 2565/629; C12Q 2565/631
USPC .......................... 250/281, 282, 283, 284, 288
See application file for complete search history.

(56) References Cited

U.S. PATENT DOCUMENTS 3,905,886 A *  9/1975  Wang ............................ 204/532
6,548,263 B1 *  4/2003  Kapur et al. .................... 506/32
(Continued)

OTHER PUBLICATIONS

Stewart et al., Nanostructured Plasmonic Sensors, Jun. 2, 2007, Chem Rev, 2008, 108, 494-521.*
(Continued)

*Primary Examiner* — Nicole Ippolito
*Assistant Examiner* — Jason McCormack
(74) *Attorney, Agent, or Firm* — Klarquist Sparkman, LLP

(57) ABSTRACT

The present invention presents a device and methods of use thereof in combined electrohydrodynamic concentration and plasmonic detection of a charged species of interest using a flow-through nanohole array. The device comprises microchannels, which are linked to a substrate with arrays of through nanoholes, wherein the substrate comprises two layers, wherein one of the layers is made of insulator material and one of the layers is made of metal, whereby induction of an electric field across the nanohole array results in the species of interest concentrating inside the nanoholes and in the vicinity of the nanohole arrays. The induction of an electric field is achieved by means of an external electric field source, which is applied to the fluid containing the species of interest, resulting in electroosmotic (EO) flow. An additional pressure driven fluid flow in the microchannels, co-directional to the EO flow is applied by external means. The resulting fluid flow from the combination of the EO and pressure driven flow results in a total bulk fluid flow hereafter referred to as bulk flow (BF). The local electric field strength across the insulator layer of the nanoholes is high and the charged species in the fluid may exhibit a high electrophoretic (EP) velocity, opposing the BF. The local field strength in the metallic portion of the nanoholes is null, due to the conducting nature of the metal, and the charged species in the fluid exhibits a null EP velocity in this region. The BF and the EP velocity of the charged species may be balanced which may result in the concentration of the charged species inside the nanoholes and at both sides of the nanohole array. An incident light over one side of the nanohole array may result in the formation of surface plasmons (SP) at the interface of the metal and the surrounding liquid containing the concentrated species. The signal from the SP may be detected by optical means, including surface plasmon resonance (SPR) imaging and SPR spectroscopy.

24 Claims, 9 Drawing Sheets

(51) Int. Cl.
G01N 33/543 (2006.01)
B01L 3/00 (2006.01)

(56) References Cited

U.S. PATENT DOCUMENTS

| | | | |
|---|---|---|---|
| 7,351,670 B2 | 4/2008 | Hoshi et al. | |
| 2005/0148064 A1* | 7/2005 | Yamakawa et al. | 435/287.2 |
| 2006/0278580 A1* | 12/2006 | Striemer et al. | 210/650 |
| 2007/0023621 A1* | 2/2007 | Blick et al. | 250/251 |
| 2007/0125942 A1* | 6/2007 | Kido | 250/284 |
| 2009/0045333 A1* | 2/2009 | Chiarot et al. | 250/288 |
| 2009/0244532 A1* | 10/2009 | Letant et al. | 356/244 |
| 2010/0170798 A1* | 7/2010 | Sibbett et al. | 204/600 |
| 2010/0210008 A1* | 8/2010 | Strand et al. | 435/287.1 |
| 2011/0036994 A1* | 2/2011 | Frayling | 250/459.1 |
| 2011/0076665 A1* | 3/2011 | Gatenholm et al. | 435/1.1 |
| 2011/0107822 A1* | 5/2011 | Bunner et al. | 73/61.52 |
| 2011/0227558 A1* | 9/2011 | Mannion et al. | 324/71.1 |
| 2012/0021934 A1* | 1/2012 | Morozov et al. | 506/9 |
| 2012/0175515 A1* | 7/2012 | Hori et al. | 250/282 |
| 2012/0218550 A1* | 8/2012 | O'Mahony | 356/432 |
| 2012/0258544 A1* | 10/2012 | Chen et al. | 436/89 |
| 2013/0041353 A1* | 2/2013 | Shin et al. | 604/892.1 |
| 2013/0065777 A1* | 3/2013 | Altug et al. | 506/9 |
| 2013/0197420 A1* | 8/2013 | Fissell et al. | 604/6.16 |

OTHER PUBLICATIONS

Stewart et al. Nanostructured Plasmonic Sensors, Jun. 2, 2007, Chem Rev, 2008, 108, 494-521.*

Ebbesen, T.W., et al., "Extraordinary optical transmission through sub-wavelength hole arrays," Nature, 391(6668): p. 667-669, (1998).

Gordon, R., et al., "A New Generation of Sensors Based on Extraordinary Optical Transmission," Accounts of Chemical Research, 41(8): p. 1049-1057 (2008).

Sinton, D., R. Gordon, and A.G. Brolo, "Nanohole arrays in metal films as optofluidic elements: progress and potential," Microfluidics and Nanofluidics, 4(1-2): p. 107-116 (2008).

Gish, D.A., et al., "Localized surface plasmon resonance biosensor using silver nanostructures fabricated by glancing angle deposition," Analytical Chemistry, 79(11): p. 4228-4232 (2007).

Hwang, G.M., et al., "Plasmonic Sensing of Biological Analytes Through Nanoholes," IEEE Sensors Journal, 8(11-12): p. 2074-2079 (2008).

Eftekhari, F., et al., "Nanoholes as Nanochannels: Flow-through Plasmonic Sensin," Analytical Chemistry, 81(11): p. 4308-4311 (2009).

* cited by examiner

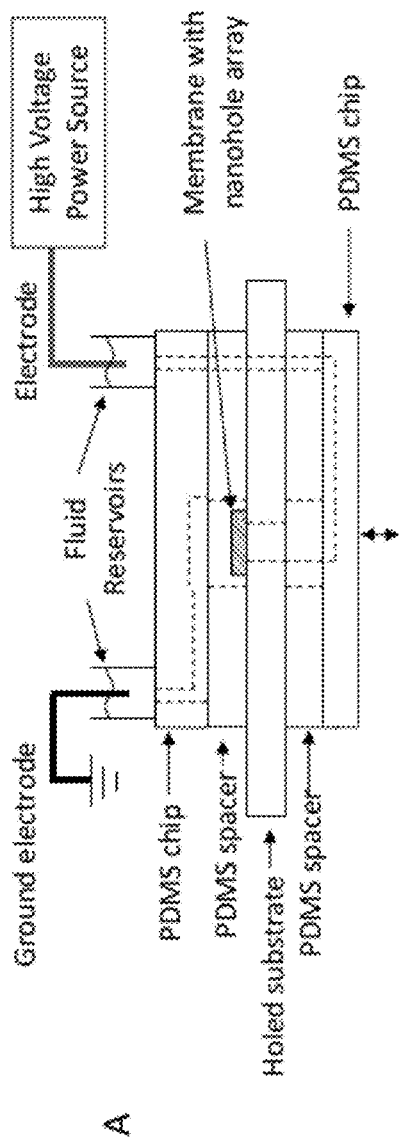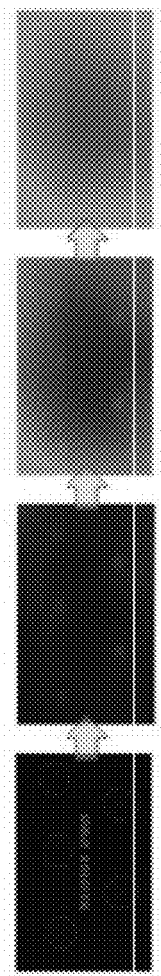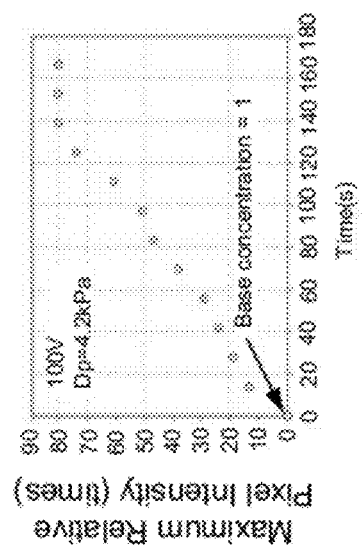
FIG. 8

FLOW THROUGH METALLIC NANOHOLE ARRAYS

FIELD

The present invention provides devices and methods of use thereof in the combined electrohydrodynamic concentration and plasmonic detection of a charged species of interest in solution, using flow-through nanohole arrays. This invention provides a combined concentration and detection device, based on electrohydrodynamic and hydrodynamic trapping of a charged species of interest in a nanohole array, and the detection of said concentrated species using a plasmonic signal generated by the same nanohole array.

BACKGROUND AND SUMMARY

Ordered arrays of nanoscale holes in metal films exhibit extraordinary optical transmission at resonant wavelengths [1,2]. Surface plasmons (SPs) are oscillating electromagnetic waves at the interface of a metal and a dielectric. Due to the confinement of the electromagnetic wave near the surface [3,4], surface plasmon resonance (SPR) has found many applications in biosensing [5,6]. In general, biosensing involves the detection of the adsorption of a biomarker to a functionalized surface [7]. In the case of SPR, the molecular adsorption may be detected directly, without a label, presenting several advantages as reported previously [8].

Incorporation of nanohole arrays in microfluidic platforms has been reported previously [9-11]. A flow-through nanohole array based sensing platform has been recently proposed [12] with several advantages over previous reported sensing schemes, such as enhanced transport of reactants via nanoconfinement and solution sieving. The use of this flow-through sensing scheme has been limited to its inherent sensing purpose with the benefits mentioned before. However, under an externally applied electric field, the metallic nature of the plasmonic sensor, comprising metallic and insulator layers, creates a localized potential gradient at the liquid-metal interface which influences the electrohydrodynamic transport of both the charged species molecules and the bulk fluid. In established electrohydrodynamic-driven microfluidic systems, the fluid may be transported by electroosmosis (EO) due to the preferential ionic distribution in the electric double layer (EDL). Charged molecules in the system are transported by electrophoresis (EP) which can oppose the EO transport of the bulk fluid depending on the molecule charge sign. Recently, Hlushkou et al. [13, 14] reported an electric field gradient focusing technique using a straight microfluidic channel with an embedded floating gold electrode. The electrode in this case, is placed normal to the electric field lines from the external circuit, resulting in the concentration of species due to the formation of sharp electric field gradients in the microfluidic channel. However, a metallic element placed in series with the microfluidic system, like the case of a nanohole array based sensor, will conduct the current and will drop the local electric field within the metal region. This will cause a null contribution of the EO and EP driving forces on the bulk and the charged species on the metallic portion of the sensor, where the fluid is transported only by the advective force from the EO flow in the microfluidic channel. On the other hand, the local electric field strength in the nitride portion of the sensor will be higher and will produce a higher EP contribution. The species may then become quasi-stationary and, therefore, locally concentrated inside the nanoholes.

Unlike the prior art, where nanoholes are used as passive elements only for sensing, the present invention disclose the use of nanohole arrays as active elements for achieving both concentration and sensing of a desired species.

The present invention is directed to apparatus and methods of operation that are further described in the next Brief Description of The Drawings, the Detailed Description of the Invention, and the claims. Other characteristics and advantages of the present invention will become evident from the following detailed description of the invention made with reference to the accompanying drawings.

According to representative examples, apparatus comprise a voltage source coupled to apply a voltage to a substrate having a nanohole array, wherein application of a voltage is operative to concentrate and to sense charged species contained in a surrounding fluid. In typical examples, the nanohole array comprises a plurality of through holes defined in a substrate that comprises two or more layers. A microfluidic channel is fluidically coupled to the nanohole array. In some examples, the substrate with the nanohole array is placed so as to divide the microfluidic channel into two portions, wherein the two portions are fluidically coupled by the nanoholes. Two electrodes are provided that are coupled to the voltage source, wherein at least a portion of each of the two electrodes is situated in the microfluidic channel so as to apply a voltage from the voltage source to the fluid. In some examples, the first layer is made of a metal or a semiconductor material, and the second layer is made of an insulator. In other examples, the substrate comprises a plurality of layers, wherein at least one layer is made of a metal and at least one layer is made of an insulator. In other alternatives, a plurality of nanohole arrays is coupled to the voltage source so as to be operative to concentrate and to sense charged species, molecules or particles contained in the surrounding fluid. In particular examples, the nanoholes are elliptical, rectangular, biaxial, oval, or round, and the nanoholes have diameters of between 1 nm and 1000 nm. According to representative examples, a period of the nanohole array is equal to or greater than a nanohole diameter. In representative embodiments, the thickness of the metallic layer and the insulator layer are between 1 nm and 1000 nm. In a particular embodiment, the metal layer is a gold film and the insulator layer is a silicon-based material such as silicon nitride. The gold film can be formed by a thermal process such as evaporation or an electrical process such as electro-deposition, or otherwise formed.

In some examples, the thickness of the gold layer is approximately 100 nm and the thickness of the silicon nitride layer is approximately 100 nm. In other examples, the substrate comprises a third layer situated between the gold layer and the silicon nitride layer, wherein the gold layer and the silicon nitride layer are adhered to the third layer. The cross section of the microfluidic channel for fluidic access can be square, irregular, round, or rectangular. In some examples, the length of the microfluidic channel is between 1 μm and 20 cm. and the microfluidic channel is defined by a ceramic material or polymer material. Typically, the microfluidic channel is defined in a material that is transparent to light at wavelengths between 300 nm and 800 nm and the electrodes are made of a semiconductor material or a metal. The electrodes can be integrated with the microfluidic channel or be separate, and the microfluidic channel can be square or round. In some examples, a light source is situated and configured to direct an incident light flux to the nanohole array and the incident light flux consists of a single wavelength or a combination of two or more wavelengths. An optical detector is configured to receive light transmitted or reflected by the nanohole array.

Methods comprise coupling a fluid to a substrate having at least one through nanohole, concentrating an analyte at or in the nanohole by applying a voltage, and detecting the concentrated analyte. In some examples, the substrate comprises a plurality of through nanoholes that can be arranged in an array, randomly arranged, or otherwise arranged. The nanoholes can have a common diameter and/or a common axial length, or a distribution of nanohole sizes can be used. Typically, nanoholes have circular cross-sections but elliptical, arcuate, oblong, rectangular, polygonal, or other shapes can be used. A distribution of two or more nanohole shapes can be used, or a common shape used. The voltage can be applied to electrodes situated at least partially in the fluid, and the concentrated analyte detected by applying an optical flux to the nanoholes and detecting the transmitted or reflected optical flux. In some example, the applied optical flux is monochromatic, but two or more wavelengths can be used and detected individually or in combination.

The foregoing and other features and advantages of the invention will become more apparent from the following detailed description, which proceeds with reference to the accompanying figures.

BRIEF DESCRIPTION OF THE DRAWINGS

FIG. 8A is a schematic representation of the experimental setup used for the electrohydrodynamic concentration of species using a nanohole array plasmonic sensor.

FIG. 8B is a series of fluorescence images demonstrating electrohydrodynamic concentration using the flow-through nanohole array apparatus.

FIG. 8C is a plot showing the maximum relative concentration of species over time from the results in 8B.

DETAILED DESCRIPTION

Figure 1:
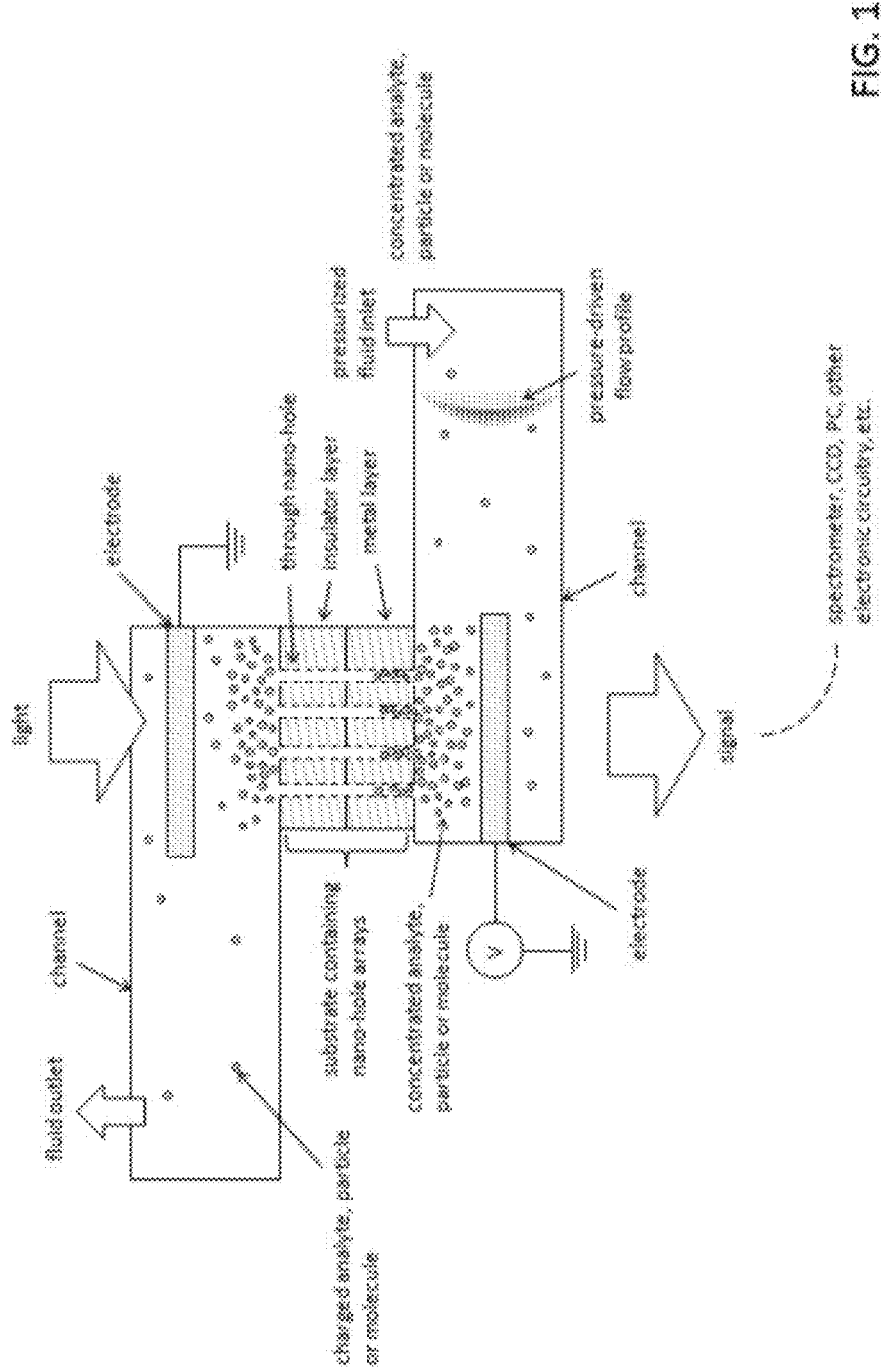
FIG. 1 illustrates an embodiment of an apparatus for the concentration and the detection of species using flow-through nanohole arrays.

A novel dual-function apparatus for performing combined concentration and sensing of charged species using a nanohole array based plasmonic sensor is presented herein. Ordered arrays of nanoscale holes in metal films exhibit extraordinary optical transmission at resonant wavelengths. Surface plasmons (SPs) are oscillating electromagnetic waves at the interface of a metal and a dielectric. Due to the confinement of the electromagnetic wave near the surface, surface plasmon resonance (SPR) has found many applications in biosensing.

In general, biosensing involves the detection of the adsorption of a biomarker to a functionalized surface. In the case of SPR, the molecular adsorption may be detected without a label, presenting several advantages. Flow-through nanohole array based sensing presents several advantages over other sensing schemes, such as enhanced transport of reactants via nanoconfinement and solution sieving. However, the use of this flow-through nanohole array has been limited to its inherent sensing purpose. Moreover, sensing techniques are usually limited by the amount of species in the sample and higher concentration of species may be required to achieve a detectable signal.

Under an externally applied electric field, the metallic nature of the nanohole array creates a localized potential gradient at the liquid-metal interface, which influences the electrohydrodynamic transport of both the charged species molecules and the bulk fluid. In established electrohydrodynamic-driven microfluidic systems, the fluid may be transported by electroosmosis (EO) due to the preferential ionic distribution in the electric double layer (EDL). Charged molecules in the apparatus are rather transported by electrophoresis (EP), which can oppose the EO transport of the bulk fluid depending on the molecule charge sign. A metallic element placed in series with the microfluidic system, like the case of a nanohole array, will conduct the current and will drop the local electric field within the metal region. This will cause a null contribution of the EO and EP driving forces on the bulk and the charged species on the metallic portion of the sensor, where the fluid is transported only by the advective force from the EO flow in the microfluidic channel. On the other hand, the local electric field strength in the nitride portion of the sensor will be higher and will produce a higher EP contribution. The species may then become quasi-stationary and, therefore, locally concentrated inside the nanoholes. Sensing of the concentrated charged species may be performed using Surface Plasmon Resonance (SPR) techniques.

Any of a wide variety of types of charged species may be concentrated and sensed without leaving from the scope and spirit of the invention, included but not limited to: biological samples, chemical samples, proteins, cells, dyes, etc. In particular, the invention presented herein offers the advantage of using the same nanohole array for performing concentration and sensing of a target charged species. Concentration is particularly important in applications where the target species is present in low concentrations, such as biomedical diagnosis.

In one embodiment, this invention provides a device and methods of use thereof for the combined electrohydrodynamic concentration and plasmonic sensing of a species of interest.

In another embodiment, the invention provides a combined concentrating and sensing device comprising:
two microfluidic channels;
an array of through nanoholes;
a unit to induce an electric field across said microfluidic channels and across said array of through nanoholes;
a unit to induce a pressure driven flow in said microchannel;
a unit to induce an incident light over the array of through nanoholes;
a unit to acquire and record a plasmonic signal emitted by the array of through nanoholes;
wherein the array of through nanoholes is linked to and sandwiched between the microchannels.

FIG. 1 illustrates an embodiment of an apparatus for combined electrohydrodynamic concentration and plasmonic sensing of charged species. According to the embodiment shown in FIG. 1, a microfluidic channel is placed in contact with the metal film on the substrate containing the array of through nanoholes, hereinafter referred to as nanohole array, to transport a fluid sample containing the charged species of interest through the nanohole array. A second microfluidic channel is shown and placed in contact with the insulator film of the substrate containing the nanohole array to guide the fluid sample containing species. A plurality of microchannels may be used to supply different fluid samples containing different species through the nanohole array for combined electrohydrodynamic concentration and plasmonic detection.

A fluid, driven by pressure means, is introduced into a microfluidic channel through an inlet, filling the microfluidic channel and the through holes in the nanohole array. The pressure driven flow may be accomplished by any means well known to one with expertise in the art. An outlet is used to drive the fluid out of the microfluidic channel and maintain the pressure driven flow of the fluid across the apparatus.

Electrodes are placed in direct contact with the fluid and are externally connected to a power supply. When an electric field is applied to the fluid, by means of the electrodes placed in either the microfluidic channel or the fluid reservoirs, a localized potential gradient is created across the nanohole array. The metal layer of the nanohole array, placed in series with the microfluidic channel, conducts the electric current, dropping the local electric field strength within this layer. Conversely, at the insulator layer of the nanohole array, the local electric field strength is very high. In the microfluidic channel, the electric field strength is not null, as compared to the metal layer, but it is very small compared to that in the insulator layer. This electric field gradient may influence the electrohydrodynamic transport of both the charged species and the bulk fluid. The EP velocity of the charged species may be high in the insulator region, null in the metal region and small in the microfluidic channel. The ionic distribution at the EDL in the nanoholes and in the microfluidic channel may result in bulk fluid EO flow. The velocity of this EO flow may combine with the velocity from the pressure driven flow to result in a total bulk flow velocity (TBFV), which may have opposite direction than the EP velocity of the charged species. The TBFV and the EP velocity may be tuned so that the charged species may become quasi-stationary in the nanoholes in the metallic layer, and in the vicinity of the nanohole array. The bulk flow may keep transporting charged species towards the nanohole array which may result in species concentration inside the nanoholes in the metal layer, and in the vicinity of the nanohole array. The direction and the magnitude of any of the EO flow, the EP flow and the pressure driven flow velocities may be reversed or tuned in order to produce the same quasi-stationary effect in the charged species which may result in the species concentration in the nanoholes and in the vicinity of the nanohole array. The concentrated charged species may then be sensed using the same nanohole array.

A light from an external source may be directed over the nanohole array. A tunable light source may be used to tune the optical wavelength of the light. The light from the external light source can be composed of one or multiple wavelengths. Specifically, the light from the external light source may be generated by a halogen lamp, a mercury lamp, or a light-emitting diode (LED). The incident angle of the light and the intensity of the light may be adjusted to enable a surface plasmon resonance condition from the nanohole array. Specifically, the incident angle of the light may be controlled to obtain normal or near normal incidence condition on the nanohole array.

The incident light on the nanohole array may result in the excitation of surface plasmons at the interface of the metal and the surrounding liquid. Each nanohole has a dimension less than one wavelength of probe light to which the nanohole array is responsive to produce surface plasmons at the metal-fluid interface under a surface plasmon resonance condition. The nanohole array also may exhibit extraordinary optical transmission at (EOT) resonant wavelengths. The signal produced by the nanohole array, which may be the intensity of the transmitted light or the resonant peak wavelength, may be acquired by an acquisition module (unit) placed internally or externally in the device. Specifically, the signal from the nanohole array may be detected using spectrometers, CCDs (charge-coupled devices), digital cameras, PMTs (photomultipliers tubes), and APDs (avalanche photodiodes). As the concentration of charged species in the nanoholes and in the vicinity of the nanohole array changes over time (i.e. the species is concentrated) the characteristics of the signal may also change over time. The signal change may be detected by the same means aforementioned.

The surface plasmon resonance condition at the metal-fluid interface of the nanohole array can be controlled by a number of parameters.

The microfluidic channels in this embodiment may be made of polydimethylsiloxane (PDMS) using established photolithography procedures (see reference [15]). Microfluidic channels may also be formed directly over either the metal or the insulator films of the substrate containing the nanohole array. The microfluidic channel may also be made of other materials using other procedures, such as $CO_2$ laser ablation.

The electrodes are made of metal or semiconductor material. The semiconductor materials are silicon (Si), germanium (Ge), or group II-V compound-based semiconductors. The metals are titanium (Ti), aluminum (Al), nickel (Ni), copper (Cu), indium (In), magnesium (Mg), silver (Ag), gold (Au), or platinum (Pt) and the like. Those of skill in the art will understand there are other materials can be used as electrodes.

A computer-based simulation approach may be used to simulate the operation of the device. Specifically, the computer-based simulation of the operation of the device may be achieved by using finite element modeling, finite differences modeling or finite volume modeling.

Figure 2:
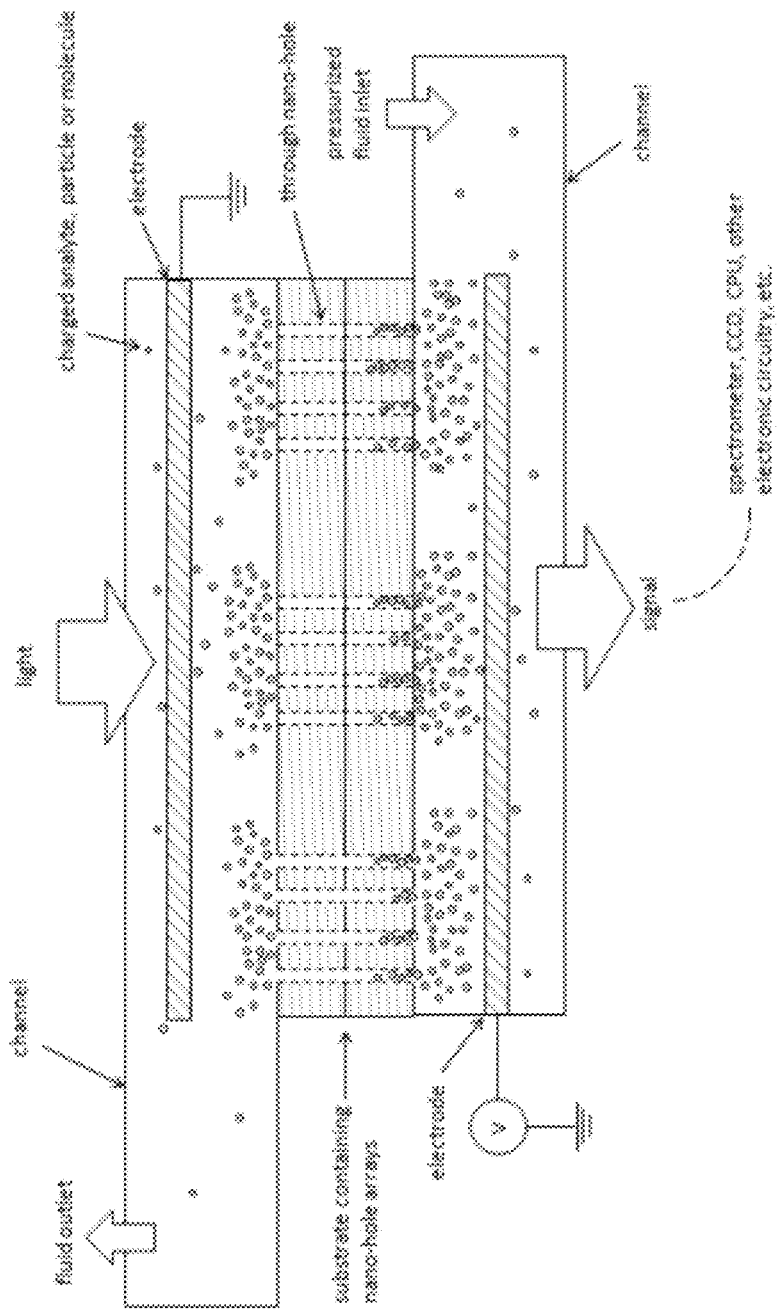
FIG. 2 illustrates an embodiment of an apparatus for the concentration and the detection of species using a plurality of flow-through nanohole arrays.

FIG. 2 illustrates an embodiment of an apparatus for combined electrohydrodynamic concentration and plasmonic sensing of charged species using multiple nanohole arrays. The concept is shown in FIG. 2 where an arrangement of nanohole arrays enables the concentration and sensing of species. The number and size of the array of nanohole arrays may be scaled to any required size. The size of the nanohole arrays may also be scaled to any required size. Moreover, the array of nanohole arrays may also be implemented such that the multiplexed concentration and sensing several species is achieved.

Figure 3:
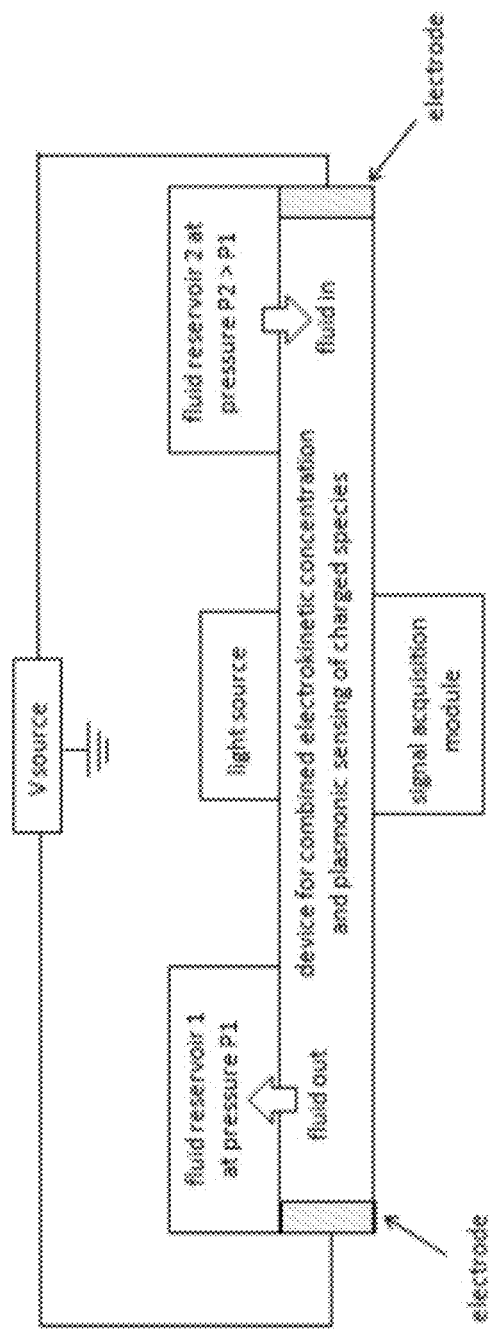
FIG. 3 illustrates an embodiment of a closed-loop system that is operative to perform concentration and the detection of species using flow-through nanohole arrays.
Figure 4:
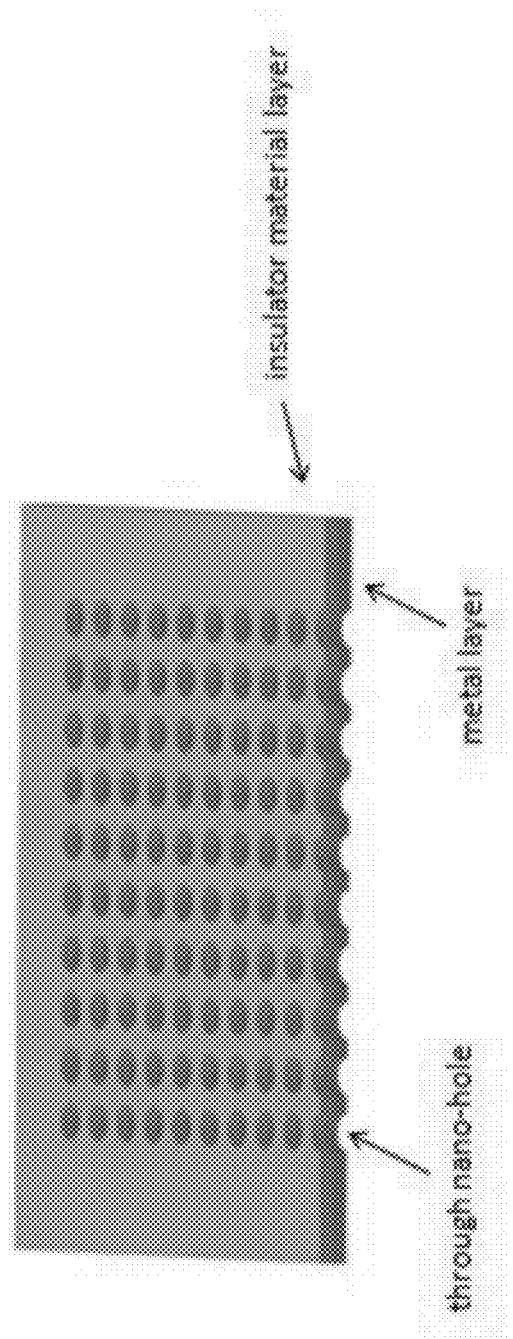
FIG. 4 is a sectional view of a schematic representation of the substrate containing a nanohole array.

FIG. 3 illustrates an embodiment of a closed-loop system that is operative to perform combined electrohydrodynamic concentration and plasmonic sensing of charged species. There are eight parts of this embodiment of the device, as shown in FIG. 4: (1) the device for combined electrohydrodynamic concentration and plasmonic sensing of charged species; (2) the fluid reservoir R1 at a pressure defined as P1; (3) the fluid reservoir R2 at a pressure P2, where P2 is a pressure greater than the pressure P1; (4) the external light source; (5) the positive electrode; (6) the negative electrode; (7) an external voltage source; and (8) the signal acquisition module. Both electrodes are immersed, partially or entirely, in the fluid in the microfluidic channel of the nanohole array based device for species concentration and sensing. The electrodes are externally connected to a voltage power source which is used to apply a voltage across the device. The fluid containing the charged species is introduced through R2 at a pressure P2 and collected in reservoir R1. The fluid in reservoir R1 is maintained at a pressure P1 which is lower than P1. The pressure difference between R1 and R2 may be generated by hydrostatic or hydrodynamic means. An exciting light source is placed over the nanohole array. The light source may be placed inside or outside the microchannel. The signal acquisition module, comprising elements for acquiring the optical signal emitted by the nanohole array is placed, either externally or internally, under the nanohole array.

The light from the external light source can be composed of one or multiple wavelengths. Specifically, the light from the external light source may be generated by a halogen lamp, a mercury lamp, or a light-emitting diode (LED). Those of skill in the art will understand that other light source can be used.

The external signal acquisition module can comprise one or more elements for the acquisition, conditioning and recording of the signal from the nanohole array. Specifically, the signal acquisition module may comprise one of or a combination of the following: a probe for signal collection, a charged couple device (CCD), a camera, a data acquisition system, and a computer. The signal from the nanohole array can be measured using optical, electrical or electromagnetic means. Specifically, the signal from the nanohole array can be measured using surface plasmon resonance (SPR) techniques, including SPR imaging and SPR spectroscopy.

FIG. 4 illustrates a schematic sectional view of the nanohole array. The nanohole array may be created on a silicon-based substrate coated with a layer of metal. Specifically, the nanohole array may be created on a silicon nitride film coated with a layer of metal. Those of skill in the art will understand there are other materials can be used. The silicon nitride film may be formed on a silicon wafer (See U.S. Pat. No. 7,351,670 which is incorporated herein by reference) by chemical vapour deposition (CVD), and/or physical vapour deposition (PVD). Etching of the silicon wafer in order to obtain a stand-free silicon nitride film may be achieved by: wet etching; anisotropic wet etching; and plasma etching.

The metal coating on the silicon-based substrate may be formed by, but not limited to, any of the following techniques: sputter coating; pulsed laser deposition; cathodic arc deposition; electrohydrodynamic deposition; reactive sputtering; molecular beam epitaxy (MBE); chemical vapour deposition (CVD); plating; and chemical solution deposition (CSD). The metal coating is made of metal or semiconductor material. The semiconductor materials are silicon (Si), germanium (Ge), or group II-V compound-based semiconductors. The metals are titanium (Ti), aluminum (Al), nickel (Ni), copper (Cu), indium (In), magnesium (Mg), silver (Ag), gold (Au), or platinum (Pt).

The through nanoholes on the metal-coated silicon-based substrate may be fabricated using one of the following procedures: Electron Beam Lithography (EBL); Reactive Ion Etching (RIE); or Focused Ion Beam (FIB) Lithography. However, the method or technology used to fabricate the nanohole array is not limited to the aforementioned techniques.

The nanohole array comprises a plurality of nanoholes. The holes are round, rectangular, biaxial, elliptical, etc. The preferred embodiment is exemplified by round holes with 300 nm in diameter and 200 nm in depth, wherein the insulator layer thickness is 100 nm and the metal layer thickness is 100 nm. The periodicity of the nanohole array is 500 nm, and defined as the center-to-center distance between holes. The holes are through holes and are uniformly distributed across the metal-on-silicon substrate. The metal-on-silicon substrate utilized in the preferred embodiment is approximately 6 µm long, 6 µm wide, and 200 nm high, and the diameter, depth and periodicity of the nanoholes corresponds to a small area ratio of the nanohole array 401 to the metal-on-silicon substrate 400. This means that the small area ratio indicates that the total area of the nanoholes together compared to the total area of the silicon-based metal-coated substrate 400 is small.

Figure 5:
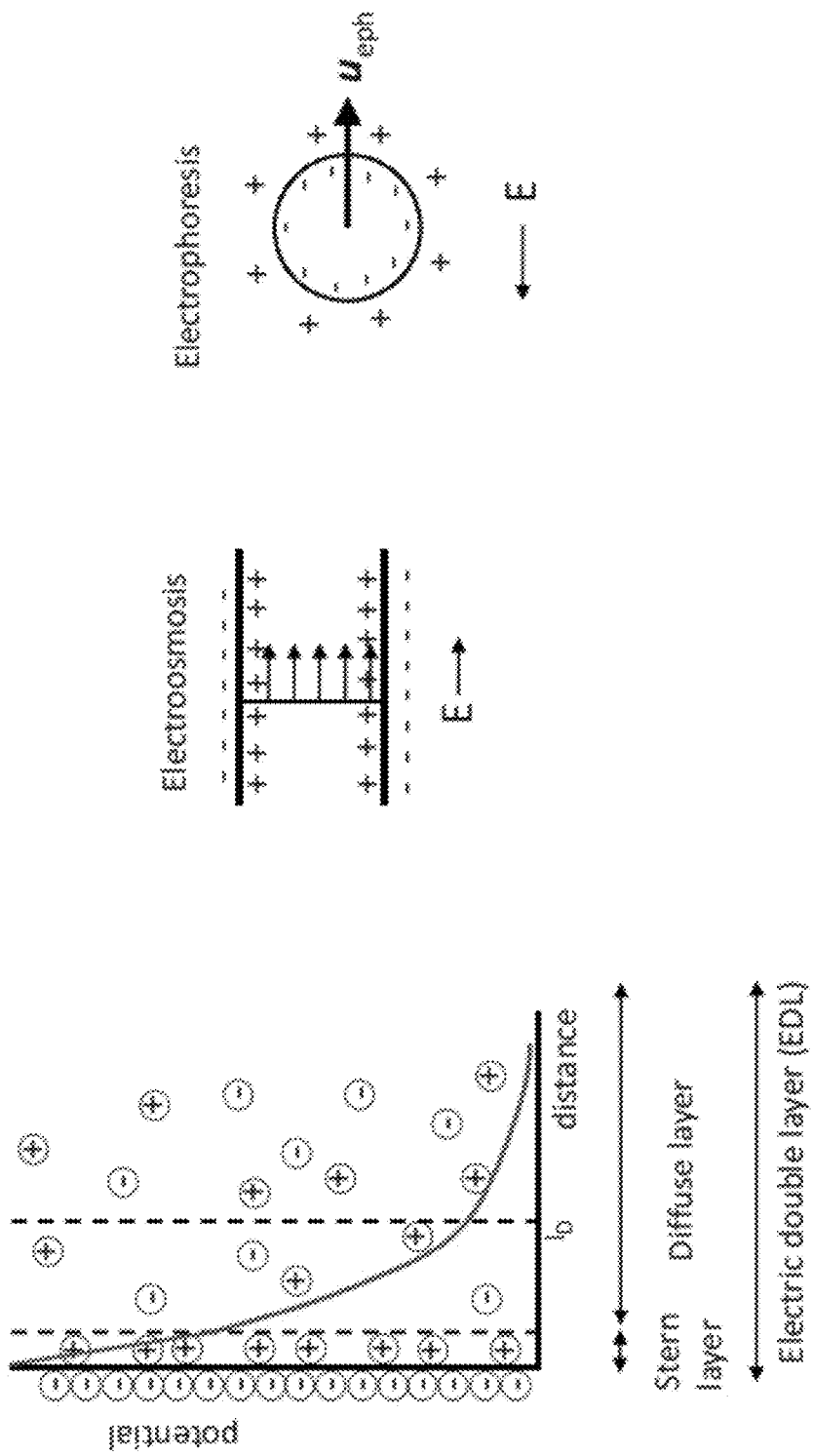
FIG. 5 is a schematic representation of an Electrical Double Layer (EDL) and the electrokinetic phenomena involved in the electrohydrodynamic concentration of charged analyte: electroosmosis and electrophoresis.

FIG. 5 illustrates the concepts of Electrical Double Layer (EDL), of electroosmosis, and of electrophoresis. Ordinarily, most materials acquire a surface electric charge whenever a liquid, or polar medium, is in contact with them [16]. Considering the sample liquid containing the species may be an electrolyte, the inner walls may acquire an electric charge when brought into contact with the sample liquid. The surface charge at the solid will influence the ionic distribution in the sample liquid (electrolyte solution) forming a charge gradient close to the solid-liquid interface. Ions with like charge (coions) are repelled from the solid surface, while ions with opposite charge (counterions) are attracted to the surface. This repulsion and attraction of ions creates a preferential distribution of ions close to the charged solid surface, which leads to the formation of an EDL. Two layers compose the EDL: the compact layer and the diffuse layer. The compact layer is formed by counterions fixed to the charged solid surface, and it is immobile. The diffuse layer is formed by an excess of counterions over coions, where all ions can move under an external applied electric field. The preferred embodiment is exemplified by a schematic representation where the acquired surface charge of the solid wall of the microchannel and the charge of the coions is negative, and the charge of the counterions is positive. The characteristic thickness of the EDL is usually referred to as the Debye length, $\lambda_D$. The electric potential at the shear surface between the charged surface and the electrolyte solution is commonly referred to as the zeta potential ($\zeta$).

Under an applied electric field, tangent to the solid-liquid interface, ions in the EDL will move towards the opposite charge electrode, from the electrodes that are used to apply the voltage. In small channels, such as the microchannels in the invention presented herein, the motion of ions can be transmitted to the rest of the sample liquid by viscous forces, resulting in electroosmotic flow (EOF). Whenever EOF is the only source of fluid motion, the velocity profile of the electroosmotic fluid flow is plug-like (flat) as shown in FIG. 5.

Charged species, such as species in a sample fluid, may acquire a net surface charge when brought into contact with a polar medium. Under an applied electric field the charged species will tend to move towards the opposite charge electrode, from the electrodes that are used to apply the voltage. The resulting motion of the charged species relative to the surrounding fluid is referred to as electrophoresis (EP) as shown in FIG. 5.

Figure 6:
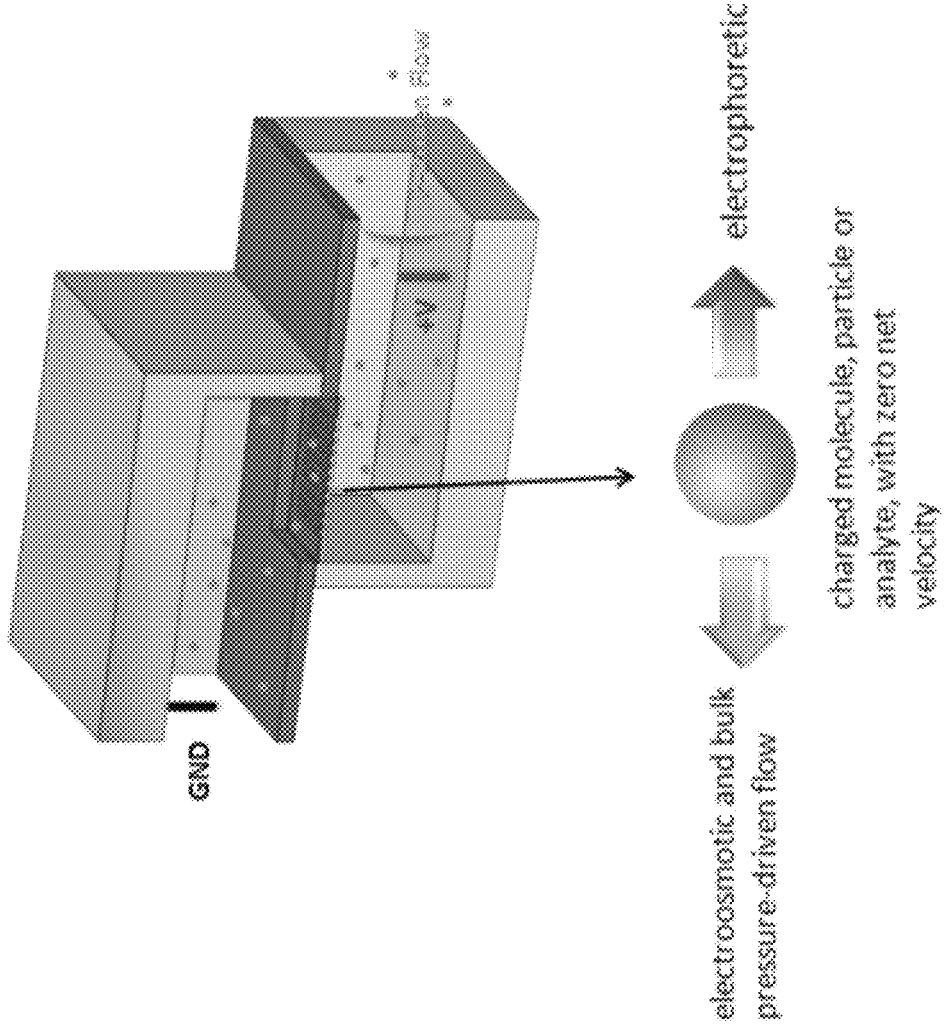
FIG. 6 illustrates the forces acting on a charged particle (species) during electrohydrodynamic concentration.

FIG. 6 illustrates a sectional view of a three-dimensional simplified schematic representation of the apparatus and details of the forces acting on the charged species. A total bulk fluid flow (TBFF) which comprises the effects of both the EO flow and the pressure driven flow, may act co-directionally, trying to drag the charged species towards one of the electrodes in the apparatus. On the other hand, the charged species also suffers an electrophoretic force (EPF) in a direction opposite to the TBFF. The magnitude of the EPF, as aforementioned, will depend on the electric field strength (EFS). The insulator region will have the strongest EFS, and the metal layer will have null EFS. Therefore, the EFS affecting the charged species will be limited to a region nearby the nanohole array (in the order of one $\lambda_D$). In distant regions from the vicinity of the nanohole array, the EPF that the charged species experiences is due to only the EFS across the microchannel which is very small compared to that across the insulator layer.

Having the EPF and the TBFF balanced, the charged species experiences a quasi-stationary condition inside the nanoholes and in the vicinity of the nanohole array. Because the fluid continues flowing through the microfluidic channels and nanoholes by means of the THF, more charged species from the fluid inlet are brought towards the nanohole array over time. The charged species transported by the bulk fluid flow from the inlet will experience a much higher EFS as they approach the vicinity of the insulator layer of the nanohole array and eventually will become quasi-stationary as well, resulting in the concentration of the charged species inside the holes and in the vicinity of the nanohole array.

Figure 7:
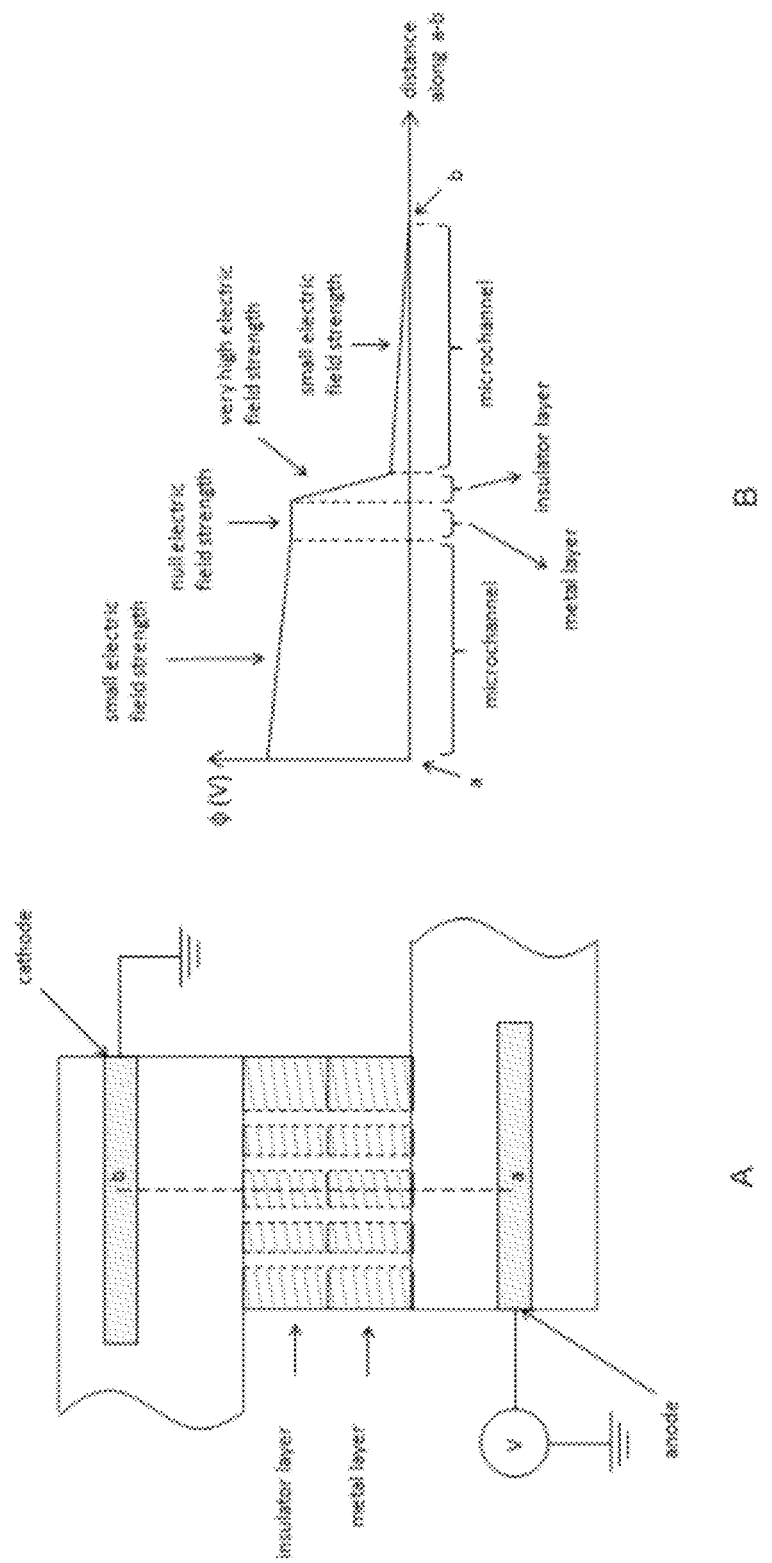
FIG. 7 is a schematic view of the electric potential drop and the electric field strengths along the device.

FIG. 7 is a schematic partial sectional view of the apparatus to perform combined electrohydrodynamic concentration and plasmonic sensing of charged species and an embodiment to exemplify the electric potential drop across the device. In the preferred embodiment (A), the voltage is applied using two platinum (Pt) electrodes placed at each side of the nanohole array, partially or totally embedded in the microchannels, and in contact with the sample liquid. The electrode below the metal side of the nanohole array is connected to a voltage source (anode), and the electrode on top of the insulator layer (cathode) is grounded. An alternative to configuration (A) wherein the polarity of the electrodes is opposite to the one shown in the embodiment may also be used to enable combined electrohydrodynamic concentration and plasmonic sensing of charged species. Additionally, external means could be used in order to exchange the polarity of the electrodes may also be used. In FIG. 7, (B) illustrates the voltage drop along line a-b in (A). The voltage drop in (B) is not to scale. The intention of (B) is to illustrate the dramatic voltage drop across the insulator layer of the nanohole array in the present invention, relative to the voltage drop along the microchannels and across the metal layer of the nanohole array. The small voltage drop along the microchannel results in a small electric field strength, compared to the high local field strength across the insulator layer of the nanohole array.

FIG. 8A illustrates a schematic representation of the experimental setup used for the electrohydrodynamic concentration of species using a nanohole array plasmonic sensor.

FIG. 8B is a series of fluorescence images demonstrating electrohydrodynamic concentration using the flow-through nanohole array apparatus. The experimental apparatus used for this experiment comprised of a substrate with 5 square arrays of through holes, as shown. For the proof-of-concept result shown in this series of images, a 1 µM fluorescein 0.25×TAE buffer solution was used, fluorescein being the charged species to concentrate. Established inverted fluorescence microscopy and imaging instrumentation, which is well known to one skilled in the art, was used for acquiring the images shown in FIG. 8B. The first image shows the initial condition, prior to the application of the electric field. A hydrostatic pressure was applied to the fluid in the apparatus via the fluid reservoirs attached to the inlet and outlet of the apparatus as depicted in 8A. The pressure applied to the fluid resulted in a pressure driven fluid flow through the microchannels and through the nanoholes. Using an external HV power source, a voltage of 100 V was then applied to the fluid containing the charged species via platinum (Pt) electrodes. The applied voltage induced local field gradients across the nanohole array, which resulted in species concentration over time, as explained before in the present invention. The series of images shows the increase of concentration from time t0 to time t4. The total time for reaching the concentration at t4, for the example in this figure, is in the order of one minute. The maximum concentration achieved at t4, as shown in FIG. 8C, was in the vicinity of the nanohole arrays and corresponds to an 80-fold increase.

FIG. 8C is a plot of the increase in fluorescein concentration over time for the conditions described in 8A and 8B.

Figure 9:
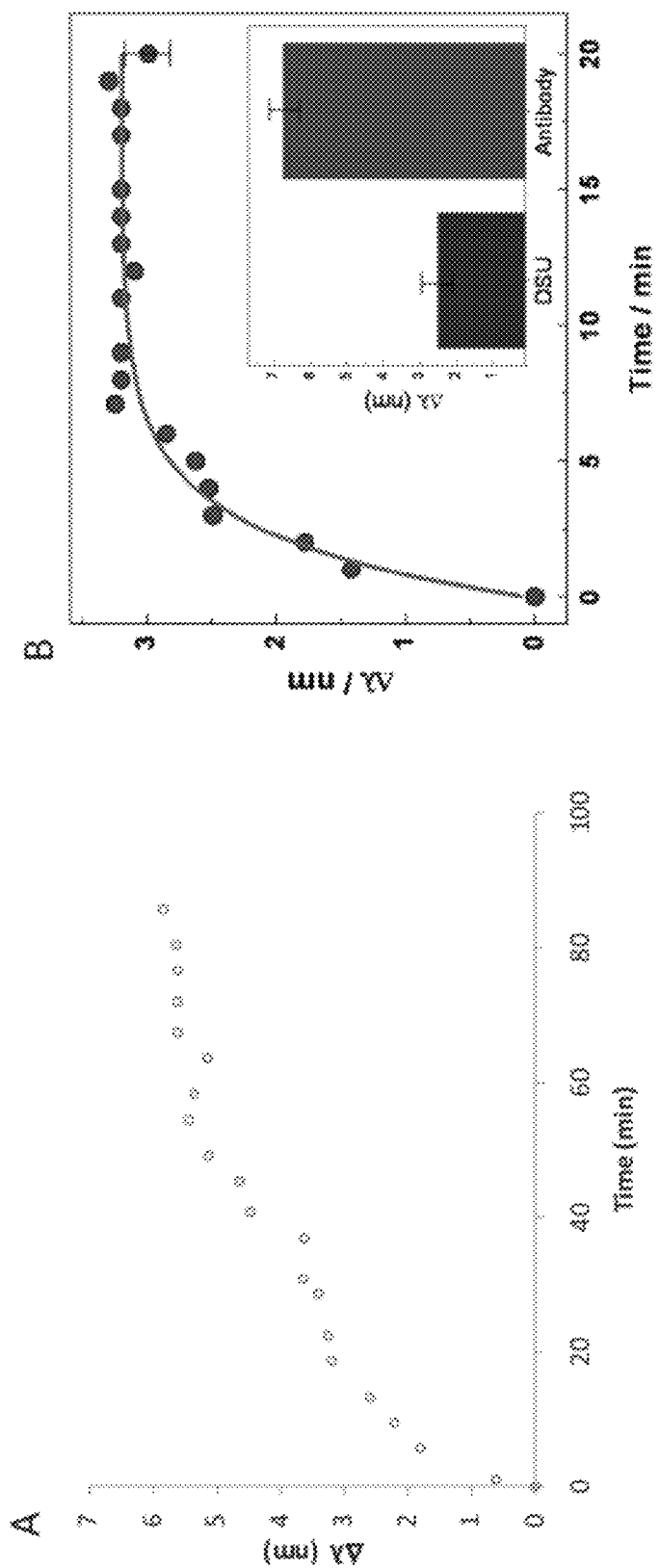
FIG. 9 illustrates the use of the apparatus for (9A) the detection of the formation of a monolayer of mercaptoundecanoic acid (MUA) and (9B) the detection of the sequential adsorption of the ovarian cancer antibody PAX8.

FIGS. 9A and 9B illustrate detection of species using an apparatus for combined electrohydrodynamic concentration and plasmonic detection. The apparatus is used to detect the monolayer formation of MUA, and the sequential adsorption of the ovarian cancer antibody PAX8.

FIG. 9A shows the response of a flow-through nanohole array with periodicity of 500 nm to MUA adsorption. Species adsorption detection is achieved by monitoring the resonant peak position in the transmission spectra. As the species is adsorbed on the surface of the plasmonic sensor the peak shift increases. At time ~60 min, the saturation of the sensor is achieved.

FIG. 9B shows the apparatus response to sequential adsorption using a flow-through nanohole array with a periodicity of 450 nm. The detection is presented as the change in resonant peak position over time as response to the sequential adsorption of DSU and ovarian cancer antibody PAX8.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

REFERENCES

1. Ebbesen, T. W., et al., *Extraordinary optical transmission through sub-wavelength hole arrays*. Nature, 1998. 391 (6668): p. 667-669.
2. Genet, C. and T. W. Ebbesen, *Light in tiny holes*. Nature, 2007. 445(7123): p. 39-46.
3. Stewart, M. E., et al., *Nanostructured plasmonic sensors*. Chemical Reviews, 2008. 108(2): p. 494-521.
4. Gordon, R., et al., *A New Generation of Sensors Based on Extraordinary Optical Transmission*. Accounts of Chemical Research, 2008. 41(8): p. 1049-1057.
5. Sinton, D., R. Gordon, and A. G. Brolo, *Nanohole arrays in metal films as optofluidic elements: progress and potential*. Microfluidics and Nanofluidics, 2008. 4(1-2): p. 107-116.
6. Homola, J., S. S. Yee, and G. Gauglitz, *Surface plasmon resonance sensors: Review*. Sens. Actuat. B, 1999. 54: p. 3-15.
7. Gish, D. A., et al., *Localized surface plasmon resonance biosensor using silver nanostructures fabricated by glancing angle deposition*. Analytical Chemistry, 2007. 79(11): p. 4228-4232.
8. Seshadri, S. R., *Attenuated total reflection method of excitation of the surface polariton in the Kretschmann configuration*. Journal of Applied Physics, 1991. 70(7): p. 3647-3654.
9. DeLeebeeck, A., et al., *On-Chip Surface-Based Detection with Nanohole Arrays*. Anal. Chem., 2007. 79(11): p. 4094-4100.
10. Hwang, G. M., et al., *Plasmonic Sensing of Biological Analytes Through Nanoholes*. Ieee Sensors Journal, 2008. 8(11-12): p. 2074-2079.

11. Lindquist, N. C., et al., *Sub-micron resolution surface plasmon resonance imaging enabled by nanohole arrays with surrounding Bragg mirrors for enhanced sensitivity and isolation*. Lab on a Chip, 2009. 9(3): p. 382-387.
12. Eftekhari, F., et al., *Nanoholes As Nanochannels: Flow-through Plasmonic Sensing*. Analytical Chemistry, 2009. 81(11): p. 4308-4311.
13. Hlushkou, D., et al., *The influence of membrane ion-permselectivity on electrohydrodynamic concentration concentration in membrane-based preconcentration units*. Lab on a Chip, 2008. 8(7): p. 1153-1162.
14. Hlushkou, D., et al., *Electric field gradient focusing in microchannels with embedded bipolar electrode*. Lab on a Chip, 2009. 9(13): p. 1903-1913.
15. McDonald, J. C., et al., *Fabrication of microfluidic systems in poly(dimethylsiloxane)*. Electrophoresis, 2000. 21(1): p. 27-40.
16. Probstein, R. F., *Physicochemical Hydrodynamics*. Second ed. 2003, New Jersey: John Wiley & Sons Inc.

We claim:

1. An apparatus, comprising:
   a substrate having at least one nanohole defined by a nanohole wall extending through the substrate, wherein the substrate and nanohole are configured to produce a plasmonic signal, wherein the substrate comprises a first layer and a second layer, the first layer and the second layer defining respective portions of the nanohole wall;
   a fluid inlet coupled to an inlet end of the at least one through nanohole and a fluid outlet coupled to an outlet end of the at least one through nanohole;
   an inlet side electrode situated at the inlet side of the at least one through nanohole and an outlet side electrode situated at the outlet side of the at least one through nanohole, wherein the inlet side electrode and the outlet side electrode are configured to apply a concentrating electric field in the at least one through nanohole;
   a pressure source configured to establish a pressure-driven fluid flow through the at least one through nanohole, wherein a fluid pressure and the concentrating field are selected to concentrate a charged species within the at least one nanohole, and the plasmonic signal is associated with the concentrated charged species in the at least one through nanohole; and
   a light source and a signal acquisition system, wherein the signal acquisition system is situated to acquire an optical signal from the at least one through nanohole in response to irradiation of the concentrated charged species in the at least one through nanohole by the light source, wherein the plasmonic signal is associated with the optical signal.

2. The apparatus of claim 1, wherein the at least one through nanohole comprises an ordered array of through nanoholes.

3. The apparatus of claim 2, wherein portions of the inlet side electrode and the outlet side electrode are situated within at least one fluid channel coupled so as to supply the pressure-driven fluid to the ordered array of through nanoholes.

4. The apparatus of claim 2, wherein the through nanoholes have a common diameter.

5. The apparatus of claim 1, wherein the first layer material is a metal or a semiconductor, and the second layer is an insulator.

6. The apparatus of claim 1, wherein the through nanoholes have elliptical, rectangular, biaxial, arcuate, circular, or polygonal cross-sections.

7. The apparatus of claim 2, wherein the at least one through nanohole comprises a plurality of nanohole arrays.

8. The apparatus of claim 7, wherein the plurality of through nanohole arrays comprises at least two arrays having different periods, different cross-sectional areas, cross-sectional shapes, or different lengths.

9. The apparatus of claim 1, wherein the diameters of the through nanoholes are between 100 nm and 1000 nm.

10. The apparatus of claim 1, wherein the period of the through nanohole array is at least about 1.2 times a through nanohole diameter.

11. The apparatus of claim 2, further comprising at least one microfluidic channel coupled to supply the pressure-driven flow to the fluid inlet.

12. The apparatus of claim 11, wherein the inlet side electrode and the outlet side electrode are situated at least partially within the at least one microfluidic channel, and the substrate is situated so as to separate the microfluidic channel into first and second portions.

13. The apparatus of claim 1, wherein the first layer material is gold and second layer material is a silicon-based insulator material.

14. The apparatus of claim 13, wherein silicon based material is silicon nitride.

15. The apparatus of claim 1, further comprising:
   at least one microfluidic channel defined by a ceramic or polymer that is optically transmissive in a wavelength range of between 300 nm and 800 nm and situated to couple the pressure-driven fluid to the fluid inlet, wherein the microfluidic channel has a square, irregular, round, or rectangular cross-section, a length of between 1 µm and 20 cm, and the substrate is situated at least partially within the microfluidic channel; and
   wherein the substrate further comprises a third layer situated between the first layer and the second layer, wherein the first layer and the second layer are adhered to the third layer.

16. An apparatus, comprising:
   a substrate having an array of through nanoholes defined therein defined by respective nanohole walls extending through the substrate, the substrate comprising a first layer and a second layer, wherein the through nanoholes extend through the first layer and the second layer such that the first layer and the second layer define respective portions of the nanohole walls;
   a microfluidic channel coupled to the array, wherein the substrate is situated so as to separate the microfluidic channel into a first portion and a second portion;
   a pressure source coupled to the microfluidic channel and configured to produce a fluid flow within the nanoholes of the array;
   first and second electrodes situated at least partially within microfluidic channel and on opposing ends of the through nanoholes of the array;
   a voltage source coupled to the first and second electrodes so as to be operative to concentrate charged species in a fluid received from the microfluidic channel in the through nanoholes based on a fluid pressure established by the pressure source; and
   a light source and a signal acquisition system, wherein the signal acquisition system is situated to acquire an optical signal from the at least one through nanohole in response to irradiation of the concentrated charged species in the at least one through nanohole by the light source.

17. The apparatus of claim 1, wherein the substrate is between 500 nm and 1000 nm thick.

18. The apparatus of claim 16, wherein the first layer is a metal or a semiconductor and the second layer an insulator, diameters of the through nanoholes are between 1 nm and 1000 nm, and a period of the nanohole array is equal to or greater than a nanohole diameter.

19. The apparatus of claim 16, further comprising an optical source configured to direct an optical flux to the nanoholes and an optical detector configured to receive a modulated optical flux associated with the concentrated charged species from the nanoholes.

20. The apparatus of claim 16, wherein the electrodes are situated on at least one surface of the microfluidic channel.

21. The apparatus of claim 16, wherein the electrodes are spaced apart from surfaces of the microfluidic channel.

22. A method, comprising:
coupling a pressure-driven fluid containing at least one analyte to an array of through nanoholes defined by nanohole walls in a substrate having a first layer that is a conductor or semiconductor and a second layer that is an insulator, wherein the nanoholes extend through the first layer and the second layer and the first layer and the second layer define respective portions of the nanohole walls;
applying a voltage so as to produce an electrical force on charged species corresponding to a fluid force on the charged species so as to concentrate a charged species in the through nanoholes; and
detecting the concentrated charged species.

23. The method of claim 22, wherein the concentrated charged species are detected based on a plasmonic signal.

24. The method of claim 22, wherein the charged species is a biological sample, a chemical sample, a protein, a cell, or a dye.

* * * * *